United States Patent

Jackson et al.

[11] Patent Number: 4,576,596
[45] Date of Patent: Mar. 18, 1986

[54] RESILIENT SHAPE-RETAINING SANITARY NAPKIN

[75] Inventors: David M. Jackson, Gwinnett County, Ga.; Billie J. Matthews, Winnebago County; S. Richard Bornslaeger, Outagamie County, both of Wis.

[73] Assignee: Kimberly-Clark Corporation, Neenah, Wis.

[21] Appl. No.: 471,582

[22] Filed: Mar. 3, 1983

[51] Int. Cl.⁴ ............................................. A61F 13/16
[52] U.S. Cl. ................................ 604/370; 604/385 R; 604/380
[58] Field of Search ............... 604/366, 370, 379, 380, 604/378, 385

[56] References Cited

U.S. PATENT DOCUMENTS 3,477,433 11/1969 Dillon .................................. 604/370
4,372,312 2/1983 Fendler et al. ...................... 604/370
4,397,644 8/1983 Matthews et al. .................. 604/370

Primary Examiner—John D. Yasko
Assistant Examiner—Sherri E. Vinyard
Attorney, Agent, or Firm—J. J. Duggan; J. P. O'Shaughnessy

[57] ABSTRACT

A sanitary napkin having an absorbent batt containing a thermoplastic material is provided. The absorbent batt is folded on itself at least on each longitudinal axis with the fold being maintained by fusing areas of the adjacent layers over the batt near the folded edge.

Also contemplated are multiple layers of absorbent formed by folding with the folds being maintained by additional fused areas.

6 Claims, 5 Drawing Figures

RESILIENT SHAPE-RETAINING SANITARY NAPKIN

FIELD OF THE INVENTION

This invention relates to a sanitary napkin, and particularly to a sanitary napkin containing thermoplastic material.

BACKGROUND OF THE INVENTION

Absorbent pads such as sanitary napkins which utilize cellulosic fiber as their principal absorbent, are well known. Cellulosic fiber provides a relatively inexpensive source of absorbent material but suffers from distinct disadvantages when utilized alone as an absorbent layer. One of the main disadvantages is that when a layer of cellulosic fiber is wet, it tends to collapse upon itself with the result that a saturated cellulosic fiber is dense, compacted, and relatively hard and uncomfortable.

This disadvantage has been recognized and thermoplastic fibers have been added to batts of cellulosic fibers in an attempt to retain the relatively inexpensive source of absorbency while introducing resistance to a permanent deformation and also resilience associated with the presence of these fibers. Representative examples of absorbent pads made with this combination of fibers can be found in U.S. Pat. Nos. 4,082,886; 4,129,132; 3,976,074; 4,054,141; 4,047,531; 3,545,441; 4,219,024; and 4,100,324. It has also been noted that when a layer of absorbent material containing thermoplastic fibers is folded upon itself, resiliency is increased even further in the sanitary product containing this folded absorbent layer.

There are difficulties inherent in using thermoplastic material in a cellulosic absorbent batt. The introduction of a thermoplastic material can decrease absorbent capacity and can also diminish the capillary attraction for the fluid to be absorbed. In order to counteract these problems, additional absorbent materials which absorb high levels of fluid per unit volume may be introduced underneath the absorbent layer or, in the case of a folded thermoplastic containing absorbent layer, the highly absorbent insert is positioned within the fold. An absorbent pad such as the one described above is described in more detail in U.S. patent application Ser. No. 266,795 filed May 26, 1981 which has been informally allowed and is hereby incorporated by reference. This particular application describes an absorbent insert made of surfactant treated meltblown microfiber.

When a sanitary napkin or the like is designed with a folded absorbent layer containing thermoplastic material and an absorbent insert is positioned within the fold, the precise positioning of the absorbent insert is important. The absorbent insert, e.g., wood pulp fluff, surfactant treated meltblown microfiber, superabsorbents, etc. performs its function of high fluid retention per unit volume due at least part to its relatively small capillary size compared to the cover. The small capillaries help to draw fluid through the upper layer and preferentially absorb fluid until the capacity of this layer is substantially utilized. If this absorbent insert was not positioned properly, or if the insert was repositioned during wear, the benefits derived from the presence of the insert would be minimized.

Recently, sanitary napkins have been designed with increasing bulk in the central napkin portion. One way of obtaining this increased bulk is by folding the absorbent layer so that an extra fold exists in the central portion of the napkin. This extra thickness, however, is difficult to maintain in the proper position.

Examples of patents describing folded absorbent layers in napkins are U.S. Pat. No. 3,667,468, 3,954,107, 3,699,966, 3,364,931. U.S. Pat. No. 3,183,909 is an example of a patent disclosing a sanitary napkin with a raised central layer.

SUMMARY OF THE INVENTION

This invention relates to absorbent pads, particularly sanitary napkins, in which an absorbent layer containing thermoplastic material is folded upon itself at least once with the folded configuration being maintained and stabilized by bonding, e.g., fusing a thermoplastic material from one layer of the fold to the other.

BRIEF DESCRIPTION OF THE DRAWINGS

The invention may more readily be understood by reference to the drawings in which.

DETAILED DESCRIPTION OF THE INVENTION

As mentioned above, the invention broadly expressed involves the maintaining of folds in an absorbent material containing fusible thermoplastic fibers or powder by fusing selected portions of the respective layers of the fold. Suitable thermoplastic fibers or powder which may be utilized are those made from polyester, polypropylene, acrylic or nylon fibers or blend. Particularly preferred are low melting point fusible fibers such as Vinyon, a vinyl chloride/vinyl acetate copolymer sold by Avtex Fibers, Inc. of New York, N.Y.; Eastman 410 amorphous or crystalline polyester fiber sold by Eastman Chemical Products, Inc., a subsidiary of Eastman Kodak Co., Kingsport, Tenn.; or Chisso ES, a bicomponent polypropylene/polyethylene fiber sold by Chisso Limited, Osaka, Japan, which due to its differential melting point for each component of the fiber may have specific advantages in certain environments.

The fusing itself can be done by a variety of means such as hot calendar embossing or by ultrasonic means, with the latter being preferred.

Fusing is preferably performed along a continuous or discontinuous line extending longitudinally along most, if not all, of the length of the sanitary napkin and is generally inset only slightly from the fold to be maintained. Since the fluid permeable wrap utilized in conventional sanitary appliances such as a sanitary napkin is made of a thermoplastic material generally helps join the cover to the absorbent layer. In the particular embodiments discussed subsequently the cover is in the form of a coextensive layer with the absorbent and as such will be part of any fused barrier formed.

It is known to form a fluid migration barriers utilizing fused lines which are continuous in nature and for this reason, such lines can be particularly beneficial when used in certain embodiments described below. This is in contradistinction to an irregular or space pattern which would not necessarily provide the more complete fluid migration barrier protection which is desirable.

While the specific embodiments discussed in this invention relates to longitudinally fused patterns, other folded patterns may also be maintained utilizing the teachings of this invention.

Figure 1:
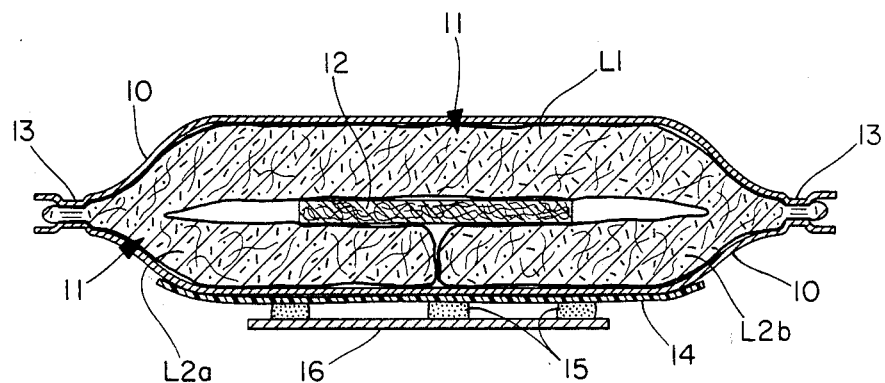
FIGS. 1, 2, 3, and 5 are end cross-sectional views of different embodiments of the subject matter of this invention.

The embodiment depicted in FIG. 1 shows a sanitary napkin having an absorbent layer 11 containing thermoplastic material wrapped by a nonwoven thermoplastic wrap 10 and folded back along itself to form a layer L1 and forming layers L1 a top layer, and L2a and 2b bottom folded layers which abut each other near the central portion of the napkin. A thin extra absorbent layer 12 is positioned within the fold and the folding end position of the absorbent layer 12 is maintained due to ultrasonic sealing lines 13 which extends substantially along the entire length of the pad near each longitudinal edge. The sanitary napkin has a fluid impermeable baffle 14 positioned on the bottom side of layers 2a and 2b. Three lines of garment attachment adhesive 15 are attached to the baffle along with a release liner 16.

A secondary fluid permeable wrap may be utilized to encircle all of the components except for the adhesive lines 15 and the release liner 16 if desired.

Figure 2:
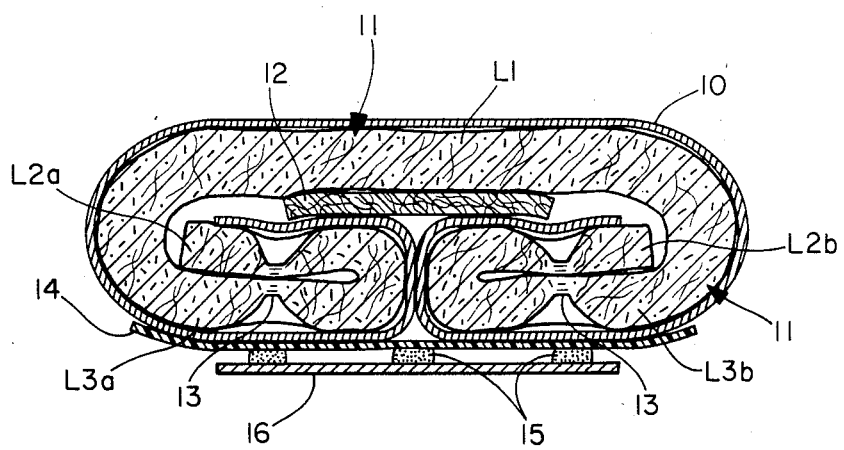

A second embodiment is shown in FIG. 2 where the additional fold is present as depicted by layers 3a and 3b. The first fold in this embodiment is not tacked. The secondary fold is maintained by the presence of the ultrasonic fused area as was the case with the primary fold in FIG. 1. It is possible, however, to separately fuse either layers L1 to L2 in this configuration. If fusing is done separately, it is usually desirable to fold the napkin with the layer to be fused positioned first. And then the layer not to be fused is subsequently folded. In this particular embodiment, fusing of layers L2 to L3 is desirable as a process aid. Assembly of layers L3 to L2 and maintenance of those layers would be extremely difficult without some mechanism for attachment. These additional folded layers are particularly desirable as additional comfort enhancement. It has been discovered that resistance to deformation is increased by the thickness and the number of folds present in an absorbent batt containing thermoplastic fibers.

Figure 3:
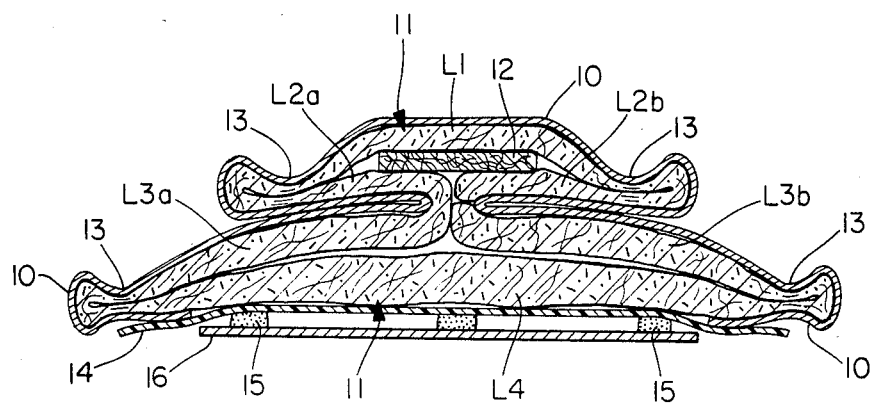

The embodiment depicted in FIG. 3 is one in which four absorbent layers are present with layers L1 and L4 not being folded. The particular configuration illustrated in FIG. 3 is one in which a raised center area is utilized. The presence of the absorbent aid 12 in FIG. 3 may be incorporated with fluid directing means or if the absorbent aid is the surfactant treated microfibrous insert described earlier, the insert itself may be used for this purpose. Multiple folded napkins with properly oriented flow directing means can provide for more even and complete utilization of absorbency with minimum amount of surface wetness and FIG. 3 with an elevated center is an example of a particular napkin configuration which has the potential to provide such utilization.

Figure 4:
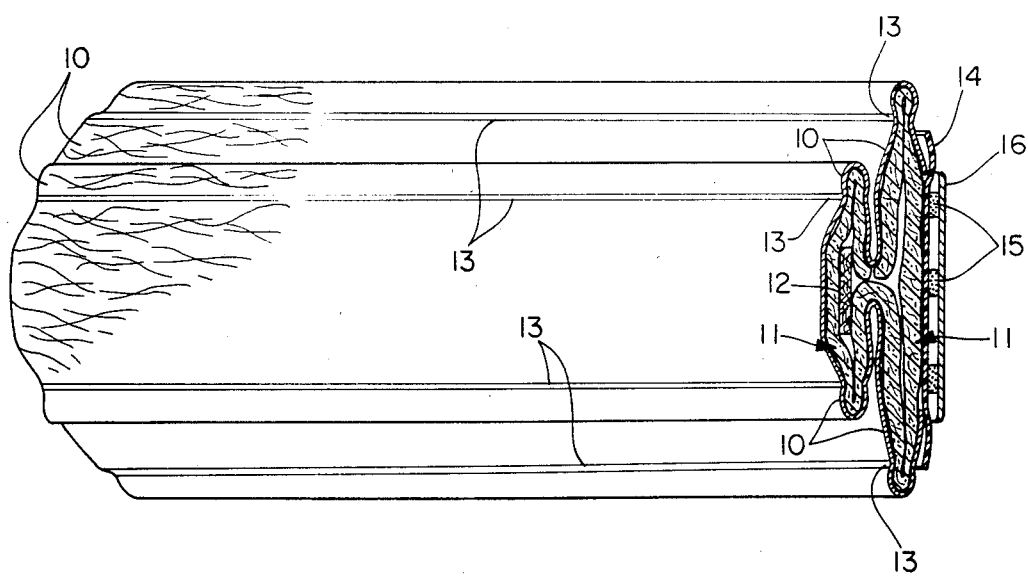
FIG. 4 is a plan view of the emnbodiment depicted at FIG. 3.

FIG. 4 is a plan view of the elevated central portion of the napkin shown otherwise at FIG. 3.

Figure 5:
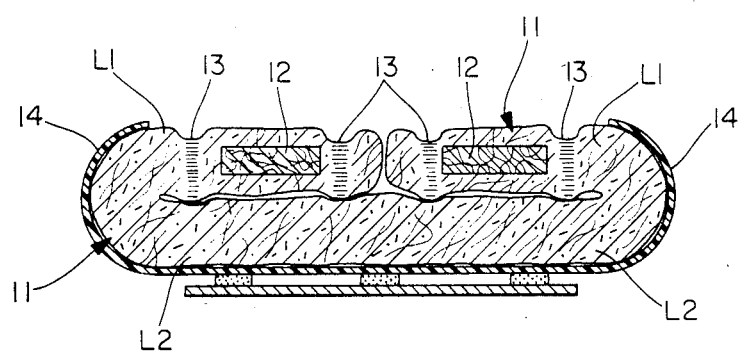

The embodiment shown in FIG. 5 provides an open central area with a single fold with the folded portion being positioned on the upper portion of the napkin. Selected fuse lines and placement of extra absorbent layer 12 provides yet another example of the combination of the folded product with fluid directing means. In this particular embodiment fluid is first contacted by only a small portion of the conventional absorbent layer 11 before it is imprisoned within the alternate absorbent layer 12. The remaining absorbent layer L1 and L2 is present initially for comfort, and secondarily, for overflow once the absorbent layer 12 is saturated. The presence of fused lines 13 are particularly beneficial for fluid barrier purposes in this particular embodiment.

It should be noted that in this figure the baffle 14 extends beyond the bottom of the napkin, up the sides, and extends partially over each upper edge in the longitudinal direction. This baffle extension can be utilized in the embodiments previously depicted and also tends to add stability to napkins containing these folded resilient layers.

An example of side compression of napkins prepared according to the embodiment shown at FIG. 2 compare with a napkin which has been folded in the same manner but the folds have not been internally attached.

EXAMPLE I

Samples for this example were prepared by trimming ½ inch from one of the longitudinal sides of the napkin. Each sample was positioned between a horizontally disposed compression apparatus having a Hunter Strain Gage with a ¼ inch diameter circular surface positioned midway along the cut side of the napkin. The uncut side of the napkin was engaged by a ¾ inch diameter compression cylinder midway along its side. (The napkin was cut to conform it to the space between the Gage and the compression cylinder but the folds and attachment were uncut.) A top weight was applied by covering the body facing side of the napkin with a lucite block 2 by 1½ inches with the 2 inch side longitudinally oriented and a weight was positioned on the block. Total weight applied to the napkin in the z direction was 128.7 gm.

Force was applied manually to the compression cylinder to comprise the napkin 15.6% in the longitudinal direction. (This was accomplished by means of a detent so that all samples were compressed equally.

This compressive force produced a reading on the Strain Gage and the comparative of those readings are set forth in the Table below. Two sets of values are presented comparing the napkin in a wet and a dry state. The napkins tested wet were treated by adding 5 ml. of a menstrual fluid analog in the center of the pad. After the fluid was absorbed a second 5 ml. aliquot was added. The napkins were held for a half hour and then tested as described above. It should be noted that the fluid chosen is felt to have specific affect on this test although the amount is similar to a heavily loaded menstrual pad.

| Pads | 1 | 2 | 3 | 4 | 5 | Conditions | Aver. | Stand. Dev. |
|---|---|---|---|---|---|---|---|---|
| | | | Folded With | | | | | |
| Bottom | 70 | 120 | 55 | 85 | 90 | dry | 84 | 24.34 |
| Baffle | 95 | 125 | 75 | 80 | 95 | wet | 94 | 19.49 |
| | | | Tacked With | | | | | |
| Bottom | 120 | 100 | 135 | 110 | 135 | dry | 120 | 15.41 |
| Baffle | 120 | 105 | 100 | 90 | 130 | wet | 109 | 15.97 |

What is claimed is:
1. A sanitary napkin comprising:
a generally planar absorbent batt containing a fusible thermoplastic component, said batt being folded upon itself a first time along a first pair of generally parallel longitudinally extending fold lines to form a first and a second layer for said napkin, and folded upon itself a second time along a second pair of generally parallel longitudinally extending fold lines to form a third layer for said napkin, said first and second layers being fixed together adjacent each of said first pair of fold lines by fusing said first and second layers along longitudinally extending fuse lines.

2. The sanitary napkin of claim 1 wherein said absorbent batt has a longitudinal center line and a pair of longitudinal side edges, each of said first pair of fold lines being spaced a sufficiently small distance from a respective side edge to form a G-shaped axial cross-section to said batt on either side of said center line when said batt is folded upon itself said second time, said napkin thereby having only three layers, said first pair of fold lines and associated fuse lines being located internally of said sanitary napkin through such folding.

3. The sanitary napkin of claim 7 wherein said absorbent batt when folded upon itself a second time forms said third layer and a fourth layer, and further including a longitudinally extending fuse line adjacent each of said second pair of fold lines to fix said third and fourth layers together.

4. The sanitary napkin of claim 3 wherein said first and second layers are co-terminous along said first pair of fold lines and form a double thickness top layer for said napkin, and said third and fourth layers are co-terminious along said second pair of fold lines and form a double thickness bottom layer for said napkin which is wider than said top layer.

5. The sanitary napkin of claim 2 or 4 further including an insert of material having a higher absorbency than said batt which is located between two of said layers.

6. A sanitary napkin comprising:
a generally planar absorbent batt containing a fusible thermoplastic component, said batt having a pair of longitudinal side edges and being folded upon itself along a pair of generally parallel longitudinally extending fold lines to form a first and a second layer for said napkin with said side edges generally meeting in the middle of said napkin, two inserts of material having a higher absorbency than said batt carried within said batt, each insert being located adjacent and extending along a respective side edge of said batt such that said inserts are generally centered on said folded batt on either side of a midline to said napkin, and a pair of longitudinally extending fuse lines associated with each insert, with a respective insert located between its pair of fuse lines.

* * * * *

UNITED STATES PATENT AND TRADEMARK OFFICE
CERTIFICATE OF CORRECTION

PATENT NO. : 4,576,596
DATED : March 18, 1986
INVENTOR(S) : Jackson et al.

It is certified that error appears in the above-identified patent and that said Letters Patent are hereby corrected as shown below:

Column 2 line 24 "emnbodiment" should read "embodiment"

Column 2 line 68 "relates" should read "relate"

Column 5 line 15 "7" should read "1"

Signed and Sealed this

Twenty-eighth Day of October, 1986

[SEAL]

Attest:

DONALD J. QUIGG

Attesting Officer

Commissioner of Patents and Trademarks